US010296719B2

(12) United States Patent
Ekin

(10) Patent No.: US 10,296,719 B2
(45) Date of Patent: May 21, 2019

(54) SMART PILL DISPENSER

(71) Applicant: EKIN TEKNOLOJI SANAYI VE TICARET ANONIM SIRKETI, Istanbul (TR)

(72) Inventor: Akif Ekin, Istanbul (TR)

(73) Assignee: EKIN TEKNOLOJI SANAYI VE TICARET ANONIM SIRKETI, Istanbul (TR)

(*) Notice: Subject to any disclaimer, the term of this patent is extended or adjusted under 35 U.S.C. 154(b) by 48 days.

(21) Appl. No.: 15/442,714

(22) Filed: Feb. 27, 2017

(65) Prior Publication Data
US 2017/0357775 A1    Dec. 14, 2017

(30) Foreign Application Priority Data

Jun. 10, 2016    (TR) ................. a 2016 07917

(51) Int. Cl.
  *G06F 19/00*        (2018.01)
  *A61J 7/00*         (2006.01)
  *G07F 17/00*        (2006.01)
  *A61J 7/04*         (2006.01)

(52) U.S. Cl.
  CPC ........ *G06F 19/3462* (2013.01); *A61J 7/0084* (2013.01); *A61J 7/0454* (2015.05); *A61J 7/0481* (2013.01); *G07F 17/0092* (2013.01); *A61J 2200/30* (2013.01); *A61J 2205/10* (2013.01); *A61J 2205/70* (2013.01)

(58) Field of Classification Search
  CPC .............. G06F 19/3462; G07F 17/0092; A61J 7/0454; A61J 7/0084; A61J 7/0481; A61J 2200/30; A61J 2205/10; A61J 2205/70

USPC ................................................ 700/231–244
See application file for complete search history.

(56) References Cited

U.S. PATENT DOCUMENTS

| | | | | |
|---|---|---|---|---|
| 2,343,496 | A * | 3/1944 | Carroll .................... | A23N 4/06 198/382 |
| 2008/0283542 | A1* | 11/2008 | Lanka ................. | G06F 19/3462 221/6 |
| 2010/0256808 | A1* | 10/2010 | Hui ....................... | G07F 7/025 700/225 |
| 2011/0087367 | A1* | 4/2011 | Gadini ............... | A47L 15/4454 700/231 |
| 2014/0025199 | A1* | 1/2014 | Berg ..................... | G07F 11/005 700/232 |
| 2014/0324216 | A1* | 10/2014 | Beg ...................... | G06Q 20/322 700/232 |
| 2014/0358278 | A1 | 12/2014 | Zhang et al. | |
| 2015/0083742 | A1* | 3/2015 | Choi .................. | B65B 69/0058 221/7 |
| 2015/0090733 | A1 | 4/2015 | Park | |
| 2016/0042151 | A1* | 2/2016 | Akdogan .............. | B25J 9/1697 700/240 |
| 2016/0143813 | A1* | 5/2016 | Cano ......................... | A61J 7/02 221/1 |

* cited by examiner

*Primary Examiner* — Michael Collins
(74) *Attorney, Agent, or Firm* — Gokalp Bayramoglu

(57) ABSTRACT

The invention is related to a smart pill dispenser which is used in a household, on a desktop, by keeping the different types of and different dosed medication inside the container, which provides information to the user in order for the user to take his/her medication in time and in correct doses and which can inform the user interactively communicate with smart devices and such as cell phones, and smart watches.

16 Claims, 2 Drawing Sheets

SMART PILL DISPENSER

CROSS REFERENCE TO RELATED APPLICATIONS

This application claims priority to Turkish application No. TR 2016/07917 filed on Jun. 10, 2016, the entire contents of which are incorporated herein by reference.

TECHNICAL FIELD

The invention is related to a smart pill dispenser which is used in a household, on a desktop, by keeping the different types of and different dosed medication inside the container, which provides information to the user in order for the user to take his/her medication in time and in correct doses and which can inform the user interactively communicate with smart devices and such as cell phones, and smart watches.

BACKGROUND

In our day, the amount of the pill usage rate continues to increase in line with the increase of the diseases. Some patients need to take more than one pill at different hours of the day. There are some difficulties encountered by the patients for taking and tracking such pills. The regular use of the pills plays an important role in the treatment and cure of the disease process. A lot of factors such as difficulties arising due to daily life, stress, forgetfulness, elderliness prevent the patients from taking their pills on the right time and correct dose. Some patients may even take the same pill twice since they might not remember that they already took their pill. There are several illiterate patients or patients who are confused on which pills to take. Such situations encountered in respect of pill usage extend the treatment process and may lead to the progression of the disease. In particular, it creates a major problem for people with chronic diseases.

The systems that are being used currently, have containers for the pills and have functions which give audio and visual alert in due course in respect of such containers. Unfortunately, these systems cannot inform the users for taking their pills when they are outside. Moreover such systems do not have a function which enables the separation of different types of pills automatically and also such systems do not record any user data and provide reports.

Other pill dispensers require the pills to be removed from the blister pack and to placed into a container. This is not a hygienic and easy use for the user.

The patent application with the publication number US 20140358278 can be given as an example in this respect. This patent application is related to an automatic pill dispenser having a structure which does not include a camera. Counting of the pills is performed with the aid of sensors and timers. A system which provides information via smart watch or smart phone is not available.

The patent application with the publication number US2015090733A1 can also be given as an example in this respect. The problem with this patent application is that the system mentioned allows the user to press the skip button to skip pill usage if the user does not want to take a pill. Therefore, any user to press the skip button by mistake or leaving the usage of the skip button on the users' discretion causes the users not to take their pills regularly and such problems also extend the treatment process. Furthermore, this system does not issue the patient's health status and regular pill usage report and does not allow monitoring and controlling the status of the patient even after months or years by the patients' relatives.

The pill dispensers currently used do not have systems which control and record the pills and dose information with camera. Furthermore, in most systems the pills are individually placed in separate containers by hand and when it is time for any pill to be taken, the light of the container thereof is on and this leads the user to take his pills There are no precautions such as hygienic environment or child lock and reporting is not provided.

A smart pill dispenser is developed in order to eliminate the disadvantages mentioned above and said invention has different technical specifications and operating modes compared to even the closest prior art practices.

SUMMARY OF THE INVENTION

The Smart Pill Dispenser is a system developed in order to aid individuals using pills to ease their life and to enable them to have a better quality of life. By means of the smart pill dispenser, it is aimed to prevent situations such as forgetfulness or neglection of users by providing the users with the right pill on time and under control.

The objective of this invention is to introduce a smart pill dispenser which ensures the patients on pills, to take their pills regularly and on time and to track said usage.

Another objective of this invention is to introduce a system which automatically places the different types and sizes of the pills in blister packs, etc into the container.

Another objective of this invention is to introduce a system which sends an alert to the smart phones and/or smart watches regarding the information of the pills which are ready to use in the container after both the pills and the doses are checked by a camera.

Another objective of the invention is to introduce a system which enables reports regarding the daily and/or weekly pill usage of the patient.

Another aim of the invention is to provide a system by defining the pills in cylindrical form on themselves by an RF code or a barcode and thereby informing the pharmaceutical warehouses which serve homes with tablets through a network by giving a smart pill dispenser usage instruction.

Another objective of the invention is to introduce a system which ensures that the patient takes the right pill with the correct dose.

The present invention is related to a desktop smart pill dispenser to realize all the objectives as set out above and the detailed description below.

The preferred embodiment of the invention is that it has a container comprising a partition.

Another preferred embodiment of the invention is that it has a feeding unit of which bottom part is open in order to receive the stacked tablets into the dispenser from this bottom section when the user is running out of tablets.

Another preferred embodiment of the invention is that it has a pill release lever which applies force to the pills in the defined periods.

Another preferred embodiment of the invention is that it has a structure that can be used on a desktop.

Another preferred embodiment of the invention is that it is structured such that it transmits information regarding the pill to the smart watch and/or smart phone.

Another preferred embodiment of the invention is that it is structured such that it sends an alert to the smart watch and/or smart phone when the pill quantity, charge/battery level is low and/or depleted.

Another preferred embodiment of the invention is that it has a camera which actively tracks the container.

Another preferred embodiment of the invention is that the pills are placed into the dispenser in cylindrical form.

Another preferred embodiment of the invention is that it has a feeding unit which enables the pills to be placed and stored in cylindrical formed blister packs.

Another preferred embodiment of the invention is that the self descriptions of cylindrical form are shown on the RF code/barcode.

Another preferred embodiment of the invention is that it has a structure which enables the pills to be used and the doses of the same to be prepared on the system, smart phone, smart watch or PC by someone else.

Another preferred embodiment of the invention is that it has a structure which enables drugstores, pharmacies, warehouses and the user instructions to be announced to the dispenser through the network, with an ID number.

Another preferred embodiment of the invention is that it has WIFI TCPIP which ensures the observation of the patient's basic functions with a smart watch.

Another preferred embodiment of the invention is that it has rubbers positioned on the cylinder.

Another preferred embodiment of the invention is that it has camera and scales which ensure that the pills are taken at the correct dose.

Another preferred embodiment of the invention is that it has a scale positioned in the container.

Another preferred embodiment of the invention is that it has a structure which enables the fingerprints defined in advance by the users to be matched with the fingerprints used for the method of the smart pill dispenser available for desktop.

Another preferred embodiment of the invention is that it has cylinders which ensure the compression of the blister shaped tablets.

BRIEF DESCRIPTION OF THE DRAWINGS

The drawings prepared in order to better describe the smart pill dispenser introduced with this invention are defined below.

Figure 1:
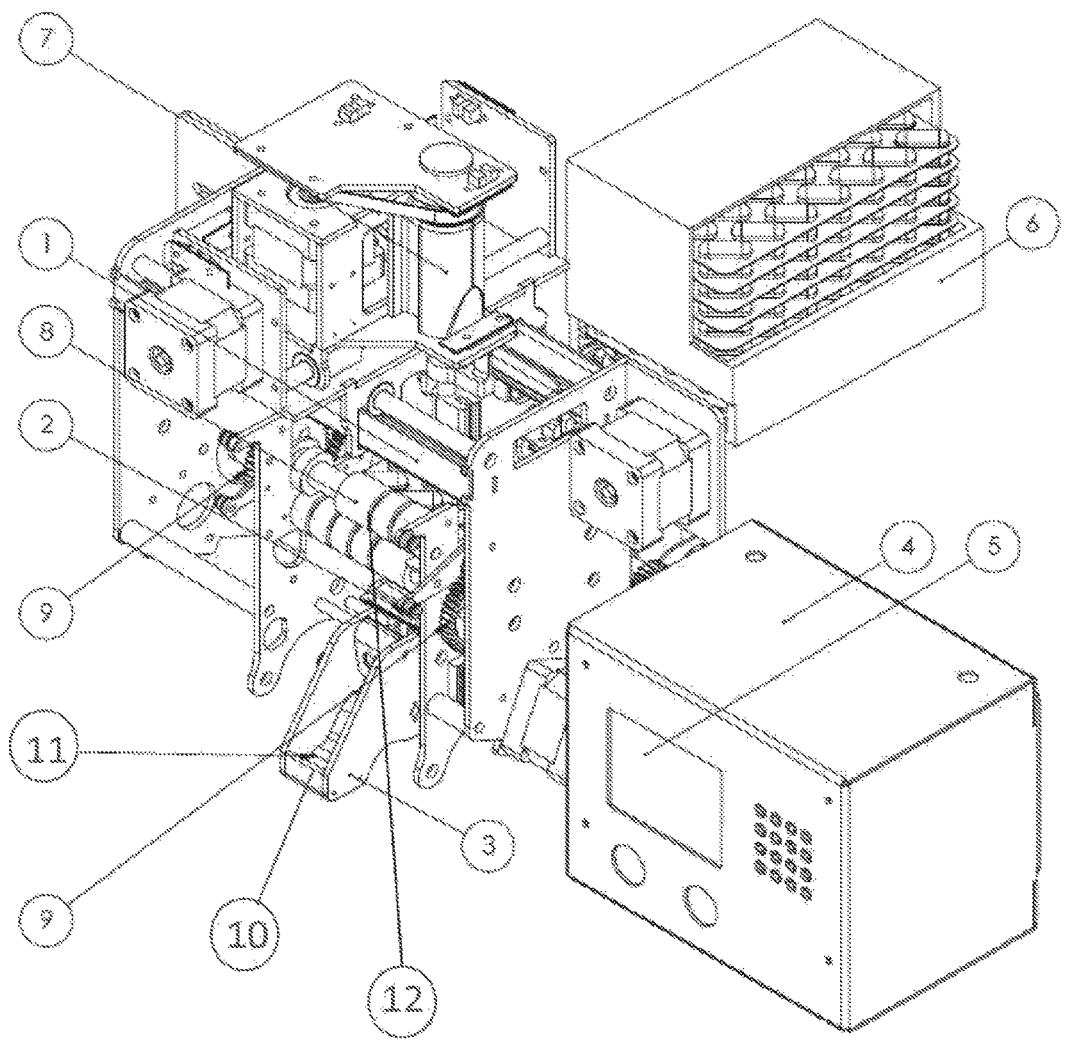
FIG. 1 is the general view of the smart pill dispenser provided herein.

The aspects/parts/pieces shown in the figures that have been prepared in order to better describe the smart pill dispenser introduced with this invention is numerated separately and the definitions of each number are provided as follows:

1. Main Body
2. Camera
3. Container
4. WIFI TCPIP
5. Lcd
6. Feeding Unit
7. Pill release Lever
8. Cylinder
9. Gear Wheel
10. Partition
11. Scale
12. Rubber

DETAILED DESCRIPTION OF THE INVENTION

In this detailed disclosure, the innovation subject to the invention smart pill dispenser is disclosed with examples only for a better understanding which will not have any restrictive influence thereon.

Desktop available smart pill dispenser basically consists of 3 main sections as follows: a section where the pills are located and stacked, a section where the mechanical parts are located and pills are removed from their tablets and provided, and the section where the information required for the system to operate is entered and all the electrical systems are located.

Since the intelligent pill dispenser device prevents the patient from accessing the pills before the time that the pills need to be taken; the patient cannot receive the drug before the designated time and therefore the patient is enabled to take his/her pills regularly, at the right time and at the correct dose. The smart pill dispenser allows the usage of various medication, as drugs having different shapes or types such as tablets etc can be identified. The medications are placed into the device in a blister and therefore they can be dispensed and taken without being touched, hygienically. A camera (2) is included in the system in order to control and record the number of pills and their dosages. As a result, the controlling of factors that need to be calculated such as checking if the different types of and differently shaped pills are available in the container and at which dose the medication needs to be taken and the number of pills to be taken.

The medications are placed into the device in a blister and therefore they can be dispensed and taken without being touched, hygienically. A camera (2) is included in the system in order to control and record the number of pills and their dosages. As a result, the controlling of factors that need to be calculated such as checking if the different types of and differently shaped pills are available in the container and at which dose the medication needs to be taken and the number of pills to be taken. By means of the smart pill dispenser when the medication is ready to be taken inside the container (3), the information is submitted by using communication technology. Therefore the information that the medication is ready to be used inside the container, is submitted to devices such as smart watches and the user's cell phone. As a result, the patient is reminded that he/she needs to take their medication and the forgetfulness of the patient is prevented. If the user has not taken his/her pill from the container (3) after a while, a signal is send to a second phone number which is different from the pre-defined phone number. If desired, by means of an additional subscription, a central unit is used which carries out tracking of medication and submitting information to users. Therefore if it is determined that the patient has not taken his/her medicine after a while, even after the signals have been sent to the smart watch, indicated primary phone number and secondary phone number, the central unit is notified and the operator at the headquarters will phone and inform the patient to take his/her medication.

By means of another feature of the smart pill dispenser if a person is using a smart watch, the values shown on the watch can be used to control the health situation of the patient and information can be monitored from the headquarters. Therefore daily and/or weekly reports can be formed for the patient. By using these reports, the relatives of the patients can track the condition of the patient through these reports.

According to another embodiment of the smart pill dispenser, the pills are not placed into the box and the medicines that are produced as strips are placed into the device as rolls. Due to the space that is gained by means of the medicines that have been placed as rolls, the device can now be produced in smaller sizes. In the system, the rolls are defined with RF codes or barcodes written on them. The dosage of the medication(s) to be taken can be carried out by a different person on a system or smart phone or PC etc. An ID or special identification number is provided for each smart device. This ID is used in order to inform the pharmacy, or pharmaceutical warehouse which delivers medication directly to the homes of patients, by giving a smart pill dispenser usage instruction via a direct network. As a result the patient is enabled to receive the correct dosage of the correct medicine at the correct time. The smart watch can be used to track down the basic functions of the patient.

The invention is a smart pill dispenser for household use that can be used on a desktop, characterized in that it comprises:

A main body (1) which carries the device construction,
A container (3) in which the pills are collected,
A camera (2) which checks if the pills have been released into the container (3),
WIFI TCPIP (4) which is the internet connection point for data exchange,
An LCD (5) screen into which all commands are inputted,
A feeding unit (6) which enables the device to be fed and which stocks the pill cartridges,
A small release lever (7) which allows the pills to be released into the container (3) by tapping the pill inside the cartridge,
A cylinder (8) which allows the blister tablets to be fixed and carried,
Gear wheels (9) which allow the the pills to be received from the feeding unit (6) using an action mechanism into the device,
A partition (10) which prevents the pill from falling out after the pill has been released into the container (3),
A scale (11) which allows the weight of the pills that have been released into the container (3) to be measured,
A rubber (12) which enables to hold the blister.

The invention is a smart pill dispenser for household use that can be used on a desktop, characterized in that the operation method of the invention is as follows:

Different types of pills such as tablets etc are identified to the device having different sizes and are placed into the device,
Daily usage and dosage information is identified by tablet identification,
The device automatically places the tablets into the container according to their usage time and shape,
The pills are placed into the device with a blister for hygienic purposes and the device only releases the pills just before usage,
A camera is integrated into the system in order to control and record the pills and dosages.
When the pills are ready in the container, information is transmitted to the cell phone or the smart watch,
If the pills are not taken from the container after a while, a notification is sent to a different phone number,
If the user desires, the user can make an additional subscription so that a notification is sent to the "headquarters" and an operator shall make a call from the "headquarters" to the user to remind the user to take his/her pill,
If a person is using a smart watch, the values shown on the watch can be used to control the health situation of the patient and information can be monitored from the "headquarters".
Daily and/or weekly reports are presented and the relatives of patients can track down their health situation.

When we take a look at the exemplary usage regarding the usage of a plurality of pills from a smart pill dispenser we can perceive that;

Pill A, is given in the morning and at night,
Pill B is given at noon,
Pill C is given in the morning, at noon and at night and according to the program the system automatically gives pill A and B in the morning, pill B at noon, and pill A and C at night.

FIG. 1, shows the general view of the smart pill dispenser. The parts that form and enable the operation of the smart pill dispenser comprises a main body (1), a camera (2), a container (3), WIFI TCPIP (4), LCD (5), feeding unit (6), release lever (7), gear wheels (9), cylinder (8), partition (10), scale (11) and rubber (12) and FIG. 1 also shows the positions of said parts in relation to each other.

Figure 2:
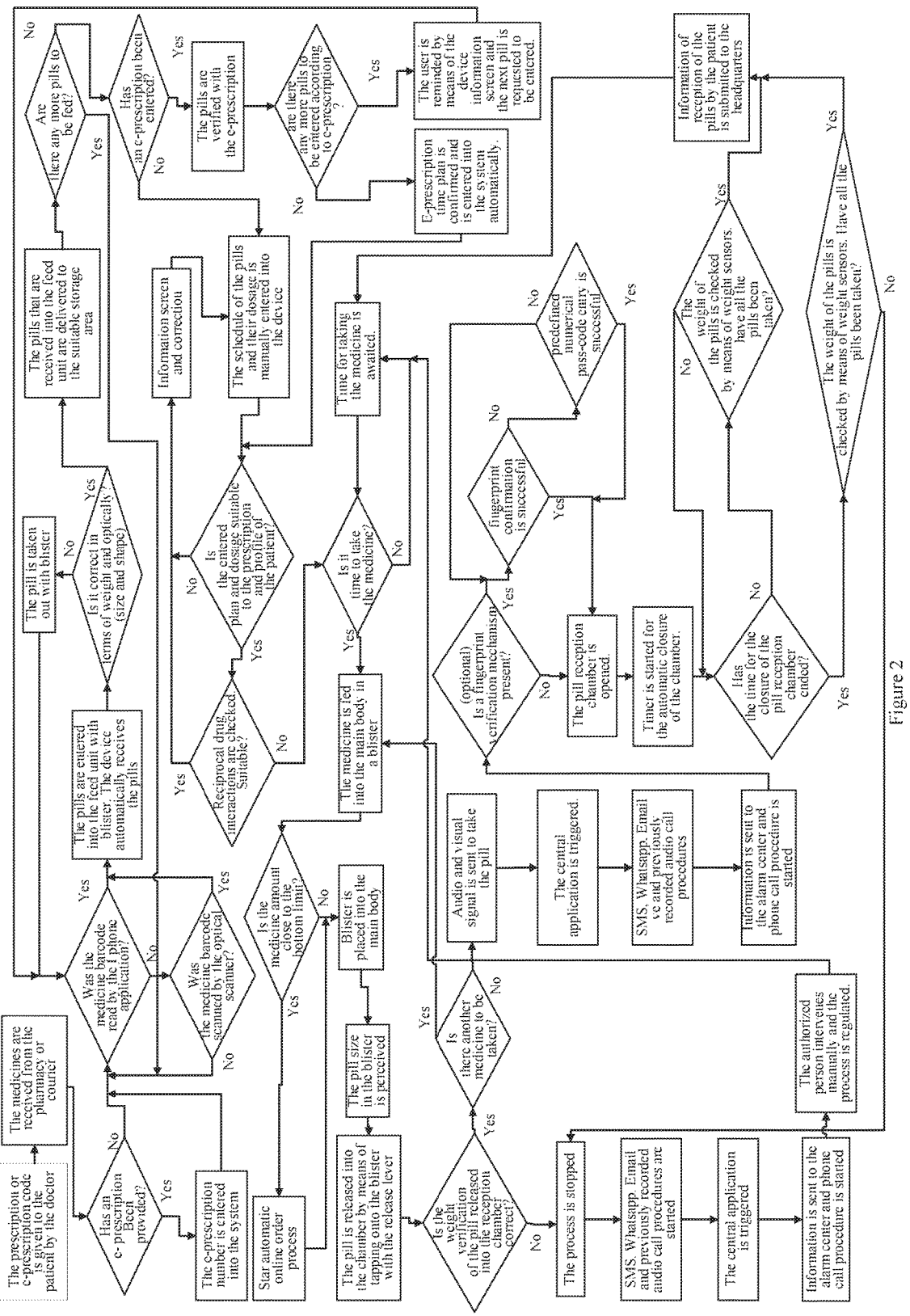
FIG. 2 is the general view of the smart pill dispenser provided herein.

FIG. 2, shows the flow diagram of the smart pill dispenser. This flow diagram shows the process steps which enable the operation of the pill dispenser. The flow diagram that is described below and in the Figure, the reading of the e-prescription and the related related barcode, can be carried out via smart phone applications such as an i-phone application. Moreover SMS, and smart phone applications such as whatsapp etc, emails and pre-recorded voice mail procedures can also be used.

A method for a smart pill dispenser that can be used on desktop wherein the method comprises the following steps:

Obtaining a prescription from the doctors or obtaining an e-prescription and receiving the medicines that have been ordered by courier,
Receiving the medicines that have been sent by courier or from the pharmacy,
Checking if an e-prescription is available or not,
If an e-prescription is present, entering the e-prescription number into the device,
Reading the barcode with an i-phone application,
If an e-prescription is not available reading the barcode with an i-phone application,
If the barcode cannot be read from an i-phone application, the barcode is read by the device,
If the barcode cannot be read from the device, the barcode is read by means of the i-phone application,
When the barcode is read from the device or from the i-phone application, the pill box is opened and the pills are placed into the feeding unit (6) with a blister and and device receives the blister automatically.
The shapes, sizes and weights of the medicines are verified,
If the medicines are not verified, the pills are taken out together with the blister and the step of barcode reading process is re-started,
When the sizes, shapes and weight of the medicines are verified, the pills are transferred to the suitable pill storage area,
Checking if any kind of medicine can be added or not,
If another medicine is to be added then the step of barcode reading is carried out,
If any kind of medicine is not going to be added it is checked if an e-prescription has been prepared or not,
If an e-prescription has been prepared before, the e-prescription is verified,
Determining if any other medicine is left in order to be added to the e-prescription,
If any other medicines are left that need to be added to the e-prescription, information is submitted on the information screen, and it is demanded for the next medicine to be prepared and the barcode reading process is carried out, If any other medicine is not going to be added into the e-prescription, a timing and dose plan shall be verified for each e-prescription and said plan is entered into the system automatically, If an e-prescription has not been prepared before, the program and the dose plan shall be entered manually, The program should check whether the dose schedule for each drug and whether the verification of the personal profile is positive or not, If the verification is not positive, a verification will be requested on the notification screen and the program and dose plan shall be entered manually, If the verification is positive, verification of any kind of cross drug effect shall be carried out, Verification of any kind of cross drug effect shall be carried out, If the verification is positive, a verification will be requested on the notification screen and the program and dose plan shall be entered manually, If the verification is negative, the next step will be taken, which is the dispensing time step, During the dispensing time step, if dispensing time has not been reached, the prescription program shall be used, and after checking if the dispensing time has been reached or not, the cycle is continued, When the dispensing time has arrived, the pills are pushed into the main body (1) of the dispenser.

It should be checked if the remaining pill amount is close to the lowest limit or not, During the controlling of the remaining pill amount, to check if said pill amount is close to the lowest limit;

If the remaining pill amounts are close to the lowest limit, an order shall be given online, before the programmed time for each pill is reached, The blister shall be safely placed, If the remaining pill amount has not reached the lowest limit, the blister shall be safely placed, Following the controlling of the remaining pill amount related to the low limit and following the safely placing of the blister, the size of the pills are checked with optical sensors, The pills are gently tapped with the release lever (7) in order to release the pills into the collection container, The weight of the pills that have been released into the container (3) is determined, If the weight of the pills that have been released into the container (3) is not positive, The process is stopped, SMS, whatsapp©, Email and pre-recorded messaging procedure is started, A notification is sent to the headquarters, The notification is submitted to the medical call centre and the procedure of calling by phone is started, The authorized people re-adjust the process manually, The prescription program is awaited, If the weight of the pills that have been released into the container (3) is positive, it is checked if another pill needs to be taken within the determined period of time, In the case that any other pill is not present in the scheduled program, If another pill is present, the pill is inserted into the pill dispenser in a blister, If any other pill is not present;

A visual and audio alert is provided in order for the pill to be taken,

A notification is sent to the headquarters,

SMS, whatsapp©, Email and pre-recorded messaging procedure is started,

The notification is submitted to the medical call centre and the procedure of calling by phone is started, Optionally it is checked if a fingerprint scanner is present or not, If a fingerprint scanner is present;

The matching of the fingerprint is checked,

If the matching is approved, the pill collection container is opened,

If there is a no-match, a pass-code that has been pre-determined shall be requested, If the correct pass-code is entered, the pill collection container is opened, If the pass-code is not correct, the fingerprint will be checked with the scanned fingerprint once again, If a fingerprint scanner is not available, The pill collection container is opened, The receiving of the pill from the container is checked, If the time to receive the pill from the container has been reached;

The reception of all pills from the weight sensor container is checked,

If all pills have not been taken, the process is stopped,

If all pills have been taken, a notification is sent to the headquarters, notifying that all pills have been taken, If the time to receive the pill from the container has not been reached;

The reception of all pills from the weight sensor container is verified,

If a verification cannot be carried out, the pill consumption status is checked, If a verification can be carried out, a notification is sent to the headquarters informing that all pills have been taken, The prescription program is awaited, The process is continued according to the dispensing time of the pills The advantages of the house-hold smart pill dispenser that can be used as a desktop are as follows;

The pills are made ready to be used at the correct time and at the correct dose, The container (3) is actively tracked, The pills that are used are kept under record, The pills are placed into the device as a roll, When the time to take the pill is reached, an audio and visual alert is sent, If the pill is not taken, remote communication is carried out, The taking of the wrong pill or carrying out wrong procedures is prevented by means of the barcode reader and pass-codes used, Prescription and e-prescription information can be obtained, Having a combined function where both the camera (2) and the scale (11) can be operated together, It enables to carry out audio message procedures, and barcode reading by means of smart phone applications, It can be tracked by the patient and his/her relatives even after months or years, It can be used regularly by continuously checking if the patient has taken his/her medication, It allows hygienic pill usage as the pills are placed in a touch free manner into the container, It can operate in compatibility with smart devices such as mobile phones and smart watches and as a result pill usage information can be submitted, It enables to prevent mistakes that can be made by a person such as forgetting to take the pills, It ensures that the patient can store and use different numbers and types of medicine, It is also enabled for the patient to be able to take different medicines with different doses at the same time, In the case that the number of pills inside the device is running low, the device carries out a pre-calculation and sends an alert to the smart watch or mobile phone, In the case that the pills are not refilled in due time, another phone that has been predetermined will be called and if the user has additional subscription, an operator from the headquarters will continue to call the user in order provide information regarding the medication to the user, In the case that the number of pills in the device are decreased or are not refilled, the device is designed such that it gives a warning to refill the dispenser and therefore the user will be less likely to forget to take his/her medicine, Both the user information and the pill information is entered onto the LCD (5) screen, As the device has a child's lock, the children are prevented from accessing the pills by mistake or by pressing any kind of button by mistake.

In the case that the charge is low and it is shown on the LCD (5) screen, the user is called on his/her mobile or an alert is sent to the smart watch, As the bottom section of the feeding unit (6) is open, the tablets that have been stacked on top of each other are received into the device, when the number of tablets decrease in time.

What is claimed is:

1. A smart pill dispenser for a household use, comprising:
a main body for carrying a device construction;
a container, where pills are collected in a touch free manner into the container;
a feeding unit which enables a device to be fed and which stocks a pill cartridge;
a small release lever configured to release the pills into the container by tapping the pill inside the pill cartridge;
a partition which prevents the pill from falling out after the pill has been released into the container;
a cylinder fixing and carrying blister tablets; and
gear wheels enable the pills to be received from the feeding unit using an action mechanism into the device.

2. The smart pill dispenser according to claim 1, wherein the container comprises the partition.

3. The smart pill dispenser according to claim 1, wherein the feeding unit includes an open bottom section to receive the pills stacked on top of each other into the device.

4. The smart pill dispenser according to claim 1, wherein the release lever applies force onto the pills at predetermined intervals of time.

5. The smart pill dispenser according to claim 1, wherein the smart pill dispenser is designed to be used on a desk top.

6. The smart pill dispenser according to claim 1, wherein the cylinder compresses the tablets.

7. The smart pill dispenser according to claim 1, further comprises a rubber placed on the cylinder.

8. The smart pill dispenser according to claim 1, further comprises a camera and a scale which enables patients to take correct pills at a correct dosage.

9. The smart pill dispenser according to claim 1, further comprises a scale positioned inside the container.

10. The smart pill dispenser according to claim 1, wherein the pills are placed into the device in a roll form.

11. The smart pill dispenser according to claim 1, further comprises a WIFI TCPIP transferring pill information to a smart watch or a mobile phone.

12. The smart pill dispenser according to claim 1, further comprises a camera configured to actively monitor the container.

13. The smart pill dispenser according to claim 11, wherein the smart pill dispenser sends an alert to the smart watch or the mobile phone in the case a pill amount, a charge or a battery is lower than a threshold value.

14. The smart pill dispenser according to claim 10, wherein the pills and dosages to be taken are arranged via a smart phone, a smart device or a PC.

15. The smart pill dispenser according to claim 10, wherein the roll has its own definitions with a RF code or a barcode.

16. The smart pill dispenser according to claim 10, wherein the device notifies usage instructions to a pharmacy or a pharmaceutical warehouse over a network using an ID number.

* * * * *